US010525010B2

(12) United States Patent
Benameur et al.

(10) Patent No.: US 10,525,010 B2
(45) Date of Patent: *Jan. 7, 2020

(54) AQUEOUS DISPERSIONS OF CONTROLLED RELEASE POLYMERS AND SHELLS AND CAPSULES THEREOF

(71) Applicant: Capsugel Belgium NV, Bornem (BE)

(72) Inventors: Hassan Benameur, Eaubonne (FR); Keith Hutchison, Bornem (BE)

(73) Assignee: Capsugel Belgium NV, Bornem (BE)

(*) Notice: Subject to any disclaimer, the term of this patent is extended or adjusted under 35 U.S.C. 154(b) by 0 days.

This patent is subject to a terminal disclaimer.

(21) Appl. No.: 14/398,177

(22) PCT Filed: Mar. 14, 2013

(86) PCT No.: PCT/EP2013/055302
§ 371 (c)(1),
(2) Date: Oct. 31, 2014

(87) PCT Pub. No.: WO2013/164122
PCT Pub. Date: Nov. 7, 2013

(65) Prior Publication Data
US 2015/0132372 A1    May 14, 2015

Related U.S. Application Data

(60) Provisional application No. 61/641,505, filed on May 2, 2012, provisional application No. 61/641,485, filed on May 2, 2012.

(51) Int. Cl.
| *A61K 9/48* | (2006.01) |
| *B29C 41/14* | (2006.01) |
| *A61K 47/10* | (2017.01) |
| *A61J 3/07* | (2006.01) |
| *B29L 31/00* | (2006.01) |

(52) U.S. Cl.
CPC .......... *A61K 9/4816* (2013.01); *A61K 9/4833* (2013.01); *A61K 47/10* (2013.01); *B29C 41/14* (2013.01); *A61J 3/077* (2013.01); *B29L 2031/7174* (2013.01)

(58) Field of Classification Search
CPC ....... A61J 3/077; A61K 47/10; A61K 9/4816; A61K 9/4833; B29L 2031/7174
See application file for complete search history.

(56) References Cited

U.S. PATENT DOCUMENTS

| 4,001,211 | A |   | 1/1977 | Sarkar |
| 4,111,202 | A | * | 9/1978 | Theeuwes ............ A61K 9/0004 |
|   |   |   |   | 206/0.5 |
| 5,264,223 | A |   | 11/1993 | Yamamoto et al. |
| 5,273,760 | A |   | 12/1993 | Oshlack et al. |
| 5,578,316 | A |   | 11/1996 | Bhardwaj et al. |
| 5,756,123 | A |   | 5/1998 | Yamamoto et al. |
| 6,451,350 | B1 |   | 9/2002 | Bartholomaeus et al. |
| 2004/0058001 | A1 |   | 3/2004 | Holzer et al. |
| 2005/0000388 | A1 |   | 1/2005 | Cho et al. |
| 2006/0165778 | A1 |   | 7/2006 | Hassan et al. |
| 2007/0053869 | A1 | * | 3/2007 | Sugiyama ............ A61K 9/4858 |
|   |   |   |   | 424/78.38 |
| 2007/0077293 | A1 |   | 4/2007 | Park et al. |
| 2007/0215511 | A1 |   | 9/2007 | Mehta et al. |
| 2007/0298095 | A1 |   | 12/2007 | Nagata et al. |
| 2008/0248102 | A1 |   | 10/2008 | Rajewski et al. |
| 2009/0004263 | A1 |   | 1/2009 | Bhatt et al. |
| 2009/0074944 | A1 |   | 3/2009 | Xie et al. |
| 2010/0113620 | A1 |   | 5/2010 | Perrie et al. |
| 2010/0158997 | A1 |   | 6/2010 | Dong |
| 2010/0260839 | A1 |   | 10/2010 | Yoshida et al. |
| 2011/0033530 | A1 |   | 2/2011 | Skalsky et al. |
| 2011/0033532 | A1 |   | 2/2011 | Angel et al. |
| 2013/0287840 | A1 | * | 10/2013 | Benameur ................ B01J 13/04 |
|   |   |   |   | 424/451 |
| 2017/0281780 | A1 |   | 10/2017 | Cape et al. |

FOREIGN PATENT DOCUMENTS

| DE | 3222476 |   | 12/1983 |   |
| EP | 0223685 |   | 5/1987 |   |
| EP | 0352800 |   | 1/1990 |   |
| EP | 0401832 |   | 12/1990 |   |
| EP | 0648487 |   | 4/1995 |   |
| EP | 0648487 | * | 4/1996 | ............... A61K 9/42 |
| GB | 643853 |   | 9/1950 |   |

(Continued)

OTHER PUBLICATIONS

International Preliminary Report on Patentability and Written Opinion for PCT/EP2013/055302 (dated Nov. 4, 2014).
International Search Report for PCT/EP2013/055302 (dated Aug. 28, 2013).
Office Action from the Canadian Intellectual Property Office for Canadian Patent Application No. 2,870,033, dated Nov. 9, 2015.
Office Action from the Japanese Patent Office for Japanese Patent Application No. 2015-509339 (w/English translation) (dated Dec. 8, 2015).
Office Action from the Japanese Patent Office for Japanese Patent Application No. 2015-509339 (w/English translation) (dated Aug. 30, 2016).
Eastman Chemical Company, "*Eastman C-A-P Enteric Coating Material (Cellulose Acetate Phthalate or Cellacefate, NF)*," Aug. 2003.

(Continued)

*Primary Examiner* — Anna R Falkowitz
(74) *Attorney, Agent, or Firm* — Klarquist Sparkman, LLP

(57) ABSTRACT

The present disclosure relates to aqueous compositions for use in the manufacture of capsule shells and capsules with a functional polymer dispersion. The present disclosure relates to aqueous compositions for use in the manufacture of capsule shells endowed with controlled release properties. The present disclosure also relates to aqueous compositions for use in the manufacture of capsule shells and capsules endowed with moisture barrier properties. The present disclosure also relates to methods of manufacturing the capsule shell and capsules, and to capsule shells and capsules obtained therewith.

10 Claims, 2 Drawing Sheets

(56) References Cited

FOREIGN PATENT DOCUMENTS

| | | | |
|---|---|---|---|
| GB | 1355324 | 6/1974 | |
| JP | S58-138458 | 8/1983 | |
| JP | H03-279325 | 12/1991 | |
| JP | H07-109219 | 4/1995 | |
| JP | 2004-131474 | 4/2004 | |
| JP | 2005-513255 | 5/2005 | |
| JP | 2005-532980 | 11/2005 | |
| JP | 5890428 | 3/2016 | |
| WO | WO80/00659 | 4/1980 | |
| WO | WO00/18377 | 4/2000 | |
| WO | WO02/102355 | 12/2002 | |
| WO | WO03/055942 | 7/2003 | |
| WO | WO2004/012701 | 2/2004 | |
| WO | WO2004/030658 | 4/2004 | |
| WO | WO2006/082842 | 8/2006 | |
| WO | WO2006/132398 | 12/2006 | |
| WO | WO 2008/050209 | * 5/2008 | ........... C08B 11/193 |
| WO | WO2008/119943 | 10/2008 | |
| WO | WO2009/050646 | 4/2009 | |
| WO | WO2009/138920 | 11/2009 | |
| WO | WO2011/155686 | 12/2011 | |
| WO | WO2012/056321 | 5/2012 | |

OTHER PUBLICATIONS

English-language translation of Notice of Reasons for Rejection issued in corresponding Japanese Patent Application No. 2013-535531, dated Jul. 7, 2015 (8 pages).

English-language translation of Search Report and Office Action issued in corresponding Chinese Patent Application No. 201180061971.1, dated Nov. 4, 2014 (13 pages).

Felton et al., "Enteric Coating of Gelatin and Cellulosic Capsules Using an Aqueous-Based Acrylic Polymer," *Pharm. Sci.* Abstract T3320 (2002).

Felton, L.A. et al., "Enteric Film Coating of Soft Gelatin Capsules," *Drug Development and Delivery*, 3(6), (Sep. 2003, posted Mar. 28, 2008).

Final Office Action from the United States Patent and Trademark Office for U.S. Appl. No. 13/827,523, dated Jun. 18, 2015.

Final Office Action from the United States Patent and Trademark Office for U.S. Appl. No. 13/881,664, dated Feb. 9, 2015.

Final Office Action from the United States Patent and Trademark Office for U.S. Appl. No. 14/496,479, dated Sep. 7, 2016.

Han et al., "In Vitro and In Vivo Evaluation of a Novel Capsule for Colon-Specific Drug Delivery," *Journal of Pharmaceutical Science*, 98(8):2626-2635 (Aug. 2009).

Huyghebaert et al., "Alternative method for enteric coating of HPMC capsules resulting in ready-to-use enteric-coated capsules," *Eur J Pharm Sci*, 21(5):617-623 (Apr. 2004).

International Search Report and Written Opinion for PCT/EP2013/055298 (dated Sep. 11, 2013).

International Search Report and Written Opinion for PCT/EP2015/068983 (dated Dec. 8, 2015).

International Search Report for PCT/IB2011/002894 (dated Jun. 4, 2012).

International Search Report from related International Application No. PCT/US2014/062210, dated Jan. 23, 2015 (5 pages).

Jain et al., "Cellulose Derivatives as Thermoresponsive Polymer: An Overview," *Journal of Applied Pharmaceutical Science*, 3(12):139-144, Dec. 31, 2013.

Kirilmaz L., "Two new suggestions for pharmaceutical dosage forms : ethylcellulose and cellulose acetate phthalate capsules," *S.T.P., Pharma Science*, 3(5):374-378 (Nov. 1993).

Office Action from the Japanese Patent Office for Japanese Patent Application No. 2015-509338 (w/English translation) (dated Nov. 8, 2016).

Office Action from the United States Patent and Trademark Office for U.S. Appl. No. 13/827,523, dated Nov. 25, 2014.

Office Action from the United States Patent and Trademark Office for U.S. Appl. No. 13/827,523, dated Jul. 1, 2016.

Office Action from the United States Patent and Trademark Office for U.S. Appl. No. 13/881,664, dated Aug. 22, 2014.

Office Action from the United States Patent and Trademark Office for U.S. Appl. No. 14/496,479, dated Sep. 16, 2015.

Office Action from the United States Patent and Trademark Office for U.S. Appl. No. 14/496,479, dated Mar. 8, 2016.

Thoma et al., "Enteric coated hard gelatin capsules," *Capsugel Technical Bulletin 1986*, 17 pages.

Written Opinion from related International Application No. PCT/US2014/062210, dated Jan. 23, 2015 (8 pages).

Extended European Search Report issued by the European Patent Office for EPC Application No. 14151265.7 dated Mar. 6, 2014.

Non-final Office action issued for U.S. Appl. No. 15/030,302 dated Aug. 10, 2017.

Notice of Reasons for Rejection issued for Japanese Application No. 2015-509339 dated Jul. 25, 2017.

\* cited by examiner

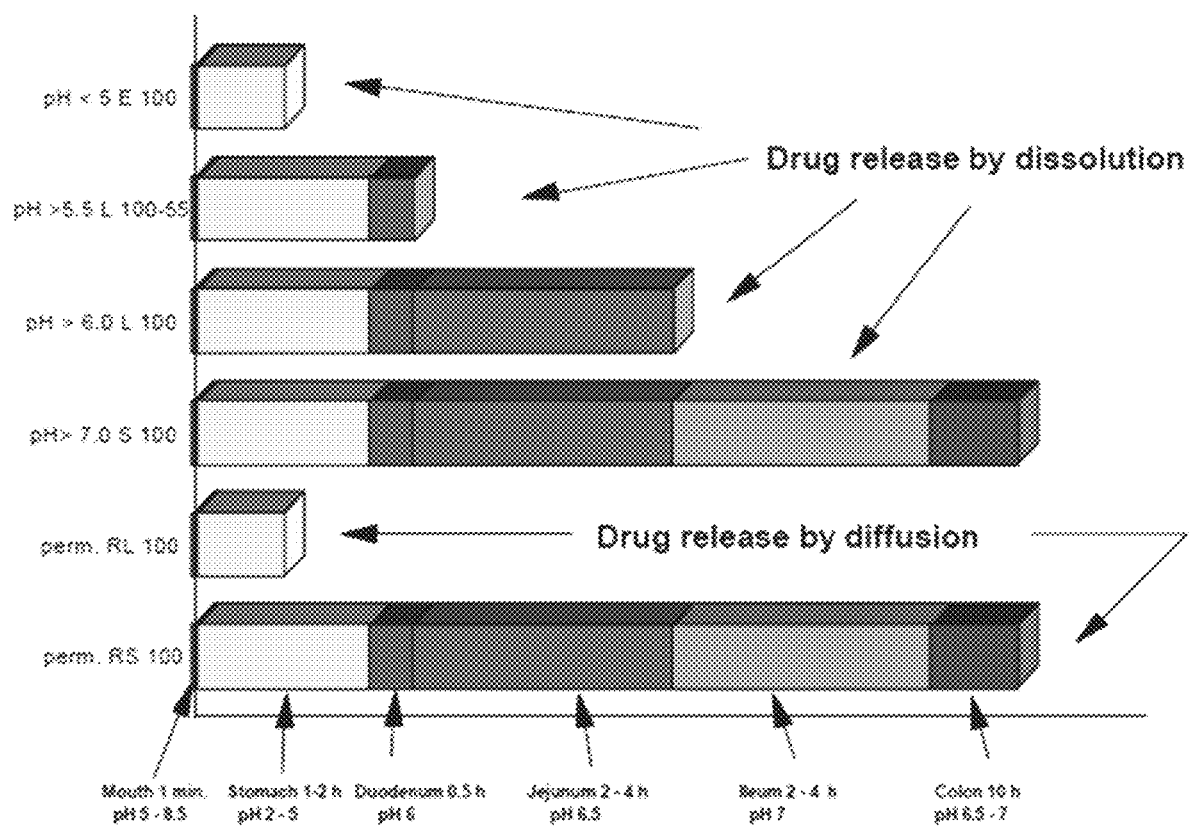
Figure 1. Controlled release profiles

Table 1 Commercially Available Aqueous Polymeric Dispersions[a]

| Brand | Type | Polymer component | Dispersion type | Additives |
|---|---|---|---|---|
| Eudragit | L30D | Copoly(MA-EA) | Latex | Tween 80 (2.1%), SDS (0.9%) |
| | RS/RL30D | Copoly(EA-MMA-TAMCl) | Pseudolatex (solvent change) | Sorbic acid, no surfactant |
| | NE30D | Copoly(EA-MMA) | Latex | PNP |
| Aquacoat | | Ethyl cellulose | Pseudolatex (solvent evaporation) | Cetyl alcohol (9%), SDS (4%) |
| Surelease | | Ethyl cellulose | Pseudolatex (phase inversion) | Dibutyl sebacate, oleic acid, ammonia, fumed silica |
| EC | N-10F | Ethyl cellulose | Powder (2.6 μm) | |
| Aquateric | | CAP | Pseudolatex | Pluronic F-68, Myvacet 9-40, Tween 80 |
| Coateric | | Poly(VAP) | Micronized powder | Plasticizer, pigments |
| Aqoat | | HPMCAS | Micronized powder (3 μm) | |

Source: Ref. 3.
[a] MA, methacrylic acid; EA, ethyl acrylate; MMA, methyl methacrylate; TAMCl, trimethylammoniomethyl methacrylate chloride; CAP, cellulose acetate phthalate; VAP, vinyl acetate phthalate; HPMCAS, hydroxypropyl methylcellulose acetate succinate; SDS, sodium lauryl sulfate; PNP, polyoxyethylene nonyl phenyl ether; Myvacet 9-40, acetylated monoglyceride.

Figure 2. Commercially Available Polymeric Dispersions

AQUEOUS DISPERSIONS OF CONTROLLED RELEASE POLYMERS AND SHELLS AND CAPSULES THEREOF

This application is a national stage entry under 35 U.S.C. § 371 of International Application No. PCT/EP2013/055302 filed on Mar. 14, 2013, which claims the priority of U.S. Provisional Application 61/641,505, filed May 2, 2012, and U.S. Provisional Application No. 61/641,485, filed May 2, 2012 all of which are incorporated herein by reference.

This application claims priority to U.S. Provisional Application 61/641,505, filed May 2, 2012, and to U.S. Provisional Application No. 61/641,485, filed May 2, 2012.

The present disclosure relates to aqueous compositions for use in the manufacture of capsule shells and capsules with a functional polymer. The present disclosure relates to aqueous compositions for use in the manufacture of capsule shells endowed with controlled release properties. The present disclosure also relates to aqueous compositions for use in the manufacture of capsule shells and capsules endowed with moisture barrier properties. The present disclosure also relates, in part, to aqueous dispersions suitable for the implementation of said manufacturing processes, and to capsule shells and capsules obtained therewith.

Capsules are well-known dosage forms that normally consist of a shell filled with one or more specific substances. The shell itself may be a soft or a hard stable shell. Hard capsule shells are generally manufactured using dip moulding processes, which can be distinguished into two alternative procedures. In the first procedure, capsules are prepared by dipping stainless-steel mould pins into a solution of polymer, optionally containing one or more gelling agents (e.g. carrageenans) and co-gelling agents (e.g. inorganic cations). The mould pins are subsequently removed, inverted, and dried to form a film on the surface. The dried capsule films are then removed from the moulds, cut to the desired length, and then the caps and bodies are assembled, printed, and packaged. See e.g., U.S. Pat. No. 5,264,223, U.S. Pat. No. 5,756,123, and U.S. Pat. No. 5,756,123. In the second procedure, no gelling agents or co-gelling agents are used and film-forming polymer solution gelifications on the moulding pins are thermally induced by dipping pre-heated moulding pins into the polymer solution. This second process is commonly referred to as thermogellation or thermogelling dip moulding. See, e.g., EP 0401832, U.S. Pat. No. 3,493,407, U.S. Pat. No. 4,001,211, GB1310697, U.S. Pat. No. 3,617,588 and WO 2008/050209. The aforementioned manufacturing processes involve the use of solutions of the different ingredients that are needed for the making the capsule shells.

Methods for the manufacturing of the soft capsule shells are also known in the art. Manufacturing of soft capsule shells at a production scale was introduced by Robert Pauli Scherer in 1933 with the invention of a rotary die encapsulation machine. The rotary die process involves continuous formation of a heat seal between two ribbons of gelatin simultaneous with dosing of the fill liquid into each capsule. Although the speed and efficiency of the manufacturing process have improved greatly in recent years, the basic manufacturing principle remains essentially unchanged. Before the encapsulation process takes place, two subprocesses are often carried out simultaneously, yielding the two components of a soft capsule: (a) the gel mass which will provide the soft capsule shell and (b) the fill matrix for the soft capsule contents.

The gel mass is prepared by dissolving the gelatin in water at approximately 80° C. and under vacuum followed by the addition of the plasticizer, for example, glycerol. Once the gelatin is fully dissolved then other components such as colors, opacifier, flavors and preservatives may be added. The hot gel mass is then supplied to the encapsulation machine through heated transfer pipes by a casting method that forms two separate gelatin ribbons each with a width of approximately 150 mm. During the casting process, the gelatin passes through the sol-gel transition and the thickness of each gel ribbon is controlled to ±0.1 mm in the range 0.5-1.5 mm. The thickness of the gel ribbons is checked regularly during the manufacturing process. The two gel ribbons are then carried through rollers, often lubricated with small quantities of vegetable oil lubricant, and onwards to the rotary die encapsulation. Each gel ribbon provides one half of the softgel. See, e.g., Aulton, M. *Aulton's Pharmaceutics: The Design & Manufacture of Medicines*, 527-533 (Kevin M G Taylor ed., 3rd ed. 2001)

Once the capsules are formed, different techniques have been used to impart controlled release properties to the hard or soft capsule shells. One such technique involves treating the surface of the pre-manufactured capsules (e.g., spraying or film-coating already manufactured capsules) with one or more layers of a substance or composition that is known to impart enteric properties. However, this technique is time-consuming, complex, and consists of expensive multiple step process. In addition, hard capsule shells made by this process must typically be pre-filled and sealed, or banded, before the surface is treated. As a result, it is not possible to use this process to make or commercialize hard capsule shells in a pre-locked status. Thus, the determination of the adequate filling parameters is left with the end user. For soft capsules, the post-treatment generally results in shells that are brittle and hard to handle.

In an attempt to overcome these drawbacks, another technique used to impart controlled release properties to hard or soft capsule shells involves the direct use of controlled release polymers (for example acid-insoluble polymers). Using this technique in the manufacture of hard capsule shells, for example, may permit the impartation of the enteric properties occurs during the manufacturing process as opposed to treating capsules which have already been pre-formed. However, use of this process for the manufacturing of hard capsule shells that meet the properties required for commercialization requires the use of a large amount of enteric polymers. At the required large amounts enteric polymers are poorly or completely water insoluble, therefore rendering the process impracticable to be used on a commercial scale. In addition, this method of coating works well on a small scale for hydroxypropyl methylcellulose (HMPC) capsules, but in the case of gelatin capsules, poor adhesion of the coat to the smooth gelatin surface can result in brittleness of the capsule. See, e.g., Huyghebaert et al., *Eur J Pharm Sci* 2004, 21, 617-623; Felton et al., *Pharm Sci* 2002, 4, Abstract T3320, and Thoma et al., *Capsugel Technical Bulletin* 1986, 1-16.

Attempts to overcome the deficiencies discussed above include (i) using low, water-soluble amounts of acid-insoluble polymers in combination with major amounts of conventional film forming polymers; (ii) salifying the water-insoluble polymers to obtain water-soluble derivatives; (iii) using solvent-based dipping solutions instead of water-based ones; and (iv) using alternative techniques which do not require polymer solubilization, such as injection moulding. See e.g., WO 2004/030658; WO2008/119943; EP1447082; U.S. Pat. No. 4,138,013; U.S. Pat. No. 2,718,667; EP 223685A1; Han et al., *Journal of Pharmaceutical*

Sciences, Vol. 98, No. 8, August 2009; and Kirilmaz L., S. T. P. *Pharma Sciences*, Nov. 10, 1993, 3/5 (374-378).

There is a need to develop a rapid, safe, and economic way to generate capsule shells displaying, for example, controlled release properties, while maintaining optimal chemical and mechanical properties, and without the need for conventional acid insoluble polymers and/or non-aqueous media, and without requiring additional processing steps, e.g., coating with the functional polymer or double dipping.

Accordingly, one aspect of the present disclosure provides aqueous compositions to make capsule shells, as well as methods of manufacture of capsule shells with the same compositions. Despite the high solid content, the aqueous compositions described herein have low viscosity when the controlled release polymer is in a dispersed state and not in solution. The low viscosity of the aqueous composition s results in advantageous manufacturing processes.

Another aspect of the present disclosure provides water-based compositions comprising cellulose derivatives polymers, polyvinyl acetate copolymers and polymetacrylate polymers that display appropriate solid content, viscosity at room temperature, setting properties, film forming and rheological behavior for use in the manufacture of hard and soft capsule shells. Another aspect of the present disclosure provides solvent-free systems obtained by emulsification polymerization technique or direct emulsification of certain polymers, known as latex and pseudo latex. In another aspect, the present disclosure relates to films and capsule shells obtained from the aforementioned water-based compositions, wherein the films and/or capsule shells display controlled release properties and exhibit optimal chemical and mechanical properties, e.g., disintegration profile, dissolution profile, film thickness, tensile strength values.

In another aspect, the present disclosure provides films and hard and soft capsule shells displaying controlled release properties, which are free of non-aqueous media/solvents.

In another aspect, the present disclosure provides rapid, economic, safe and easy to realize dip-moulding processes for the manufacture of capsule shells displaying controlled release properties. In another aspect, the present disclosure provides a rapid, economic, safe and easy to realize "one step" or "single dip" dip-moulding process for the manufacture of hard capsule shells, wherein the co-presence of conventional film-forming non enteric polymers is no longer necessary. In yet another aspect, the present disclosure provides a rapid, economic, safe and easy to realize process for the manufacture of soft capsule shells, and soft capsules, wherein the controlled release properties are imparted through the aqueous dispersion of the polymers. In another aspect, the present disclosure provides processes for the manufacture of capsules and capsule shells wherein from a layer of dispersion, bulk evaporation of water occurs while the polymer particles flocculate (pack together), then close-pack letting water-filled interstices as per continuing evaporation and particle compaction, polymer film start forming with compacted (deformed) particles, leading to inter-particles diffusion (coalescence) of polymer molecules that generate isotropic polymer film.

DESCRIPTION OF THE FIGURES

FIG. 1 shows the dissolution and disintegration profiles of capsule shells manufactured according to compositions and methods of at least one embodiment of the present disclosure.

FIG. 2. Shows some commercially available aqueous polymer dispersions.

DETAILED DESCRIPTION

As used in the present disclosure, the following words, phrases, and symbols are generally intended to have the meanings as set forth below, except to the extent that the context in which they are used indicates otherwise.

As used herein, "optional" or "optionally" means that the subsequently described even or circumstance may or may not occur, and that the description includes instances where the event or circumstance occurs and instances in which it does not.

As used herein, "w/w %" means by weight as a percentage of the total weight.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

As used herein "controlled release properties" means that the capsule shells described herein are soluble in, or disintegrated at different pH levels within the gastrointestinal tract, and that the polymers used in the dispersion are selected depending on the desired profile release. See e.g. Wen, Hong, *Oral Controlled Release Formulation Design and Drug Delivery: Theory to Practice*, (Kinam Park ed., 2010). The terms "polymer," "controlled release polymer," or "functional polymer" are polymers that impart cellulose derivative properties, polyvinyl acetate copolymers, and polymetacrylate polymers.

"Cellulose derivative polymers" refers to hydroxypropyl methylcellulose (HPMC), hydroxy-ethyl-cellulose (HEC), hydroxy-propyl-cellulose (HPC), methylcellulose (MC), sodium carboxymethylcellulose (CMCNa), ethylcellulose (EC), cellulose acetate phtalate (CAP), hydroxypropyl methylcellulose phtalate (HPMCP), hydroxypropyl methylcellulose acetate succinate (HPMCAS), and mixtures or equivalents thereof.

"Polyvinyl acetate copolymers" refers to polyvinyl acetate phtalate, polyvidone acetate, vinylpyrrolidone-vinyl acetate copolymer, polivinyl alcohol-polyethylene glycol copolymer and mixtures or equivalents thereof.

"Polymetacrylate polymers" refers to methacrylic acid/methylmethacrylate copolymers, methacrylic acid/ethylacrylate copolymers, dimethylaminocethyl methacrylate copolymers, ammoniomethacrylate copolymers, ethylacrylate/methacrylate copolymer and mixtures or equivalents thereof.

In one embodiment, the controlled release polymers are enteric polymers like polymethacrylates (copolymerisate of methacrylic acid and either methylmethacrylate or ethyl acrylate) (EUDRAGIT®), cellulose based polymers e.g. cellulose acetate phthalate (CAP, CAT, HPMCAS, HPMCP) or polyvinyl derivatives e.g. polyvinyl acetate phthalate (Coateric®.)

In one embodiment, the controlled release polymers are delayed release, pulsed, modified release polymers which are site specific delivery into the upper intestine that has been achieved for many years by the use of pH-sensitive coatings including Eudragit L100, S 100, RS, Ethylcellulose, hydroxypropylcellulose, methylcellulose, cellulose acetate, etc with or without pore formers, PLA/PGA derivatives. In one embodiment the functional polymer is suitable for colonic delivery.

The term "dispersion" refers to a two phase system where one phase consists of finely divided particles, often in a colloidal size range, distributed throughout a bulk substance. Upon application of the dispersion layer in the mold or pin used during capsule formation the colloidal particles come into direct contact with each other and form close-packed arrays due to water evaporation and the interfacial tension between water and polymer. In certain embodiments, the polymer of the aqueous dispersion is the only polymer displaying the desired controlled release properties in the aqueous compositions. Other embodiments of the present disclosure may encompass suitable polymer blends, for example blends that include dispersion inert polymers, polymer blends with other functional polymers such as polymers with moisture barrier properties, or even blends of various polymers with controlled release properties.

Unless otherwise indicated, "non-salified polymer" means that polymer free acid residues are not salified. For example, salification with carbonates, bicarbonates, hydrogen phosphates and hydroxides of elements of Groups I and II of the periodic table, or nitrogen containing base compounds (e.g., ammonia or primary, secondary or tertiary organic amines or amine derivatives), are excluded. The polymers may be non-salified in any one of the manufacturing steps of the capsule shells and capsules as described herein. Nonetheless, unwanted salification of technically irrelevant amounts of polymer may be tolerated as the result of the presence of salifying basic impurities in other ingredients used in the manufacturing processes of the capsule shells and capsules. Similarly, the presence of impurities constituting salified polymer in the purchased non-salified polymer are tolerable according to the present disclosure. Moreover, in some instances, traces or impurities of salified polymer can be present in the aqueous compositions, capsule shells or capsules of the present disclosure. In most embodiments, traces or impurities of salified polymer can be, for example, less than 1% by weight over the weight of the total polymer present.

Unless otherwise indicated, the polymers used in this disclosure are present in a dispersed state in the aqueous compositions described herein. Thus, the aqueous compositions comprise finely divided non-salified polymer solid particles having average diameters ranging from about 0.1 to about 10 microns. It will be understood that other ingredients in the aqueous compositions described herein, e.g., the processing aids, may be present in the dissolved state, dispersed state, or mixtures thereof depending on the solubility properties of the other ingredients.

The term "solids" includes at least all non-aqueous ingredients present in the aqueous compositions, capsule shells, and capsules described herein. For example, solids include all non-aqueous ingredients pre-formulated in commercially available products. Some commercially available aqueous dispersions are presented in FIG. 2.

Unless otherwise indicated, capsules described herein have the same or similar shape of commercially available, conventional capsules intended for oral administration to human or animal subjects. The hard capsules described herein can be manufactured using different processes, as well as the use of conventional equipment. For example, hard capsule shells and capsules may be generally manufactured by dipping pin moulds into an aqueous-based film forming composition and subsequently withdrawing the pins from the composition. The film formed on the moulding pins surface can then be dried, stripped off the pins and cut to a desired length, thereby obtaining the capsules caps and bodies. Normally, caps and bodies have a side wall, an open end and a closed end. The length of the side wall of each of said parts is generally greater than the capsule diameter. The capsule caps and bodies may be telescopically joined together so as to make their side walls partially overlap and obtain a hard capsule shell.

The soft capsules described herein can be manufactured using different processing and conventional equipment, and have the same or similar shape to commercially available soft capsules. For example, soft capsules may be manufactured by preparing an aqueous gel mass of the polymer in water at a suitable temperature and followed by the addition of a plasticizer. Other components such as colorants, opacifiers, flavors and preservatives may be added. The resulting gel ribbons may subsequently undergo the rotary die process.

As described herein, the term "partially overlap" is intended to encompass the side walls of caps and bodies having the same or similar length such that when a cap and a body are telescopically joined, the side wall of said cap encases the entire side wall of said body.

Unless otherwise indicated, "capsule" refers to filled capsule shells whereas "shell" specifically refers to an empty capsule. The present disclosure encompasses both hard and soft capsules, and capsule shells unless explicitly or implicitly indicated otherwise. For example in places where a method is described, and said method is known to a skilled artisan to be used exclusively in the manufacture of one type of capsules the related disclosure is to be understood within that context.

Since the hard capsule shells described herein can be filled with substances in liquid form, the hard capsules may be sealed or banded according to conventional techniques. Alternatively, the hard capsule shells can be manufactured to have a specific capsule shell design that provides certain advantages over conventional techniques, e.g., the ability to pre-lock empty caps and bodies, or completing the filling steps in a different location, or at a specific time. Examples of such designs may be found in WO 2009/138920 and WO 2009/050646.

The term "active ingredient" or "active pharmaceutical ingredient" API is used to indicate a component of the compositions, capsule shells, and capsules described herein that is pharmaceutically or physiologically active. Any compound that is pharmaceutically or physiologically active, or that may take the benefit of controlled release, is considered to be an active ingredient. As used within this disclosure the term "active ingredient formulation" or "API formulation" refers to compositions or formulations comprising at least one active ingredient, and optionally other inactive components, such as excipients, additives, etc.

In one embodiment, the present disclosure provides an aqueous composition for the manufacture of hard capsule shells, said composition comprising an aqueous dispersion of non-salified controlled release polymer, being present in an amount ranging from about 5% to about 50% by weight of the total weight of said aqueous composition; at least one processing aid present in an amount ranging from about 0.1% to about 20% by weight of the total weight of said aqueous composition, and water.

In one embodiment, the controlled release polymer is the only functional polymer present in the aqueous compositions or the described capsule shells or capsules of the present disclosure.

In one embodiment, the present disclosure provides for shells manufactured with compositions comprising an aqueous dispersion of a non-salified controlled release polymer being present in an amount ranging from about 5% to about 50% by weight of the total weight of said aqueous composition; at least one plasticizer in an amount ranging from about 6% to about 20% by weight of the total weight of said aqueous composition; at least one flocculation aid in an amount of about 0.1% to about 10% by weight of the total weight of said aqueous composition, and water in amount of about 50% to about 85% by weight of said aqueous composition. In one embodiment, the resulting shells have a composition by weight of about 50% to about 75% of the non-salified controlled release polymer, about 10% to about 40% of the plasticizer, about 1% to about 20% of the flocculation aid agent and about 0.5% to about 20% of water.

An advantage of the aqueous compositions herein is that the polymer amounts described allow for the manufacture of, for example, hard capsule shells, e.g. using a dip-moulding process, generally without the need to incorporate other film-forming polymer(s) that are conventionally used as base film-forming polymers for hard capsule shells. In other words, the aqueous dispersions and polymers of the present disclosure can be used along with the processing aids in amounts that provide films endowed with sufficient film forming properties such as thermal properties (Tg, DSC and MFT), thermo-rheological properties and mechanical properties (e.g. Young's module and brittleness). Accordingly, in one embodiment, the aqueous compositions may comprise film-forming polymer(s) conventionally used as base film-forming polymers for hard capsule shells in amounts less than about 5% by weight, e.g., less than about 1% by weight over the weight of the shell. Alternatively, in one embodiment, the aqueous compositions do not contain film-forming polymers conventionally used as base film-forming polymers for hard capsule shells. Another advantage of the aqueous compositions according to this disclosure is that the polymer amounts described allow the manufacture of, for example, soft capsules endowed with controlled release properties without the traditional post-treatment steps of, for example, coating the dried soft capsules with controlled release properties.

Examples of film-forming polymers conventionally used as base film-forming polymers for hard capsule shells include, for example, cellulose non enteric derivatives, such as HPMC (e.g. HPMC types 2910, 2906 and/or 2208 as defined in USP30-NF25), gelatin, pullulan, PVA and non enteric starch derivatives, like as hydroxypropyl starch.

In one embodiment, an aqueous composition according to the present disclosure further comprises a processing aid. In one embodiment, processing aids are selected from poloxamers or mixtures thereof. In one embodiment, the processing aid comprises a polyoxyethylene-polyoxypropylene-polyoxyethylene block polymer. The polyoxyethylene-polyoxypropylene-polyoxyethylene block polymer may comprises Poloxamer 124 (also referred herein as P124) (commercially available from BASF as KOLLISOLV™ and LUTROL® L44), Poloxamer 188 (commercially available from BASF as Pluronic® F68NF), a mixture of poloxamers 124 and 188. In one embodiment the ratios of Poloxamer 188 to Poloxamer 124 in the mixture range from 0 to about 0.9, such as from about 0.2 to about 0.9° and from about 0.7 to about 0.9. In one embodiment, the processing aid comprises a polyoxyethylene-polyoxypropylene-polyoxyethylene tri-block polymer having an average molecular weight ranging from about 1000 to about 20000.

In one embodiment, the processing aid comprises, a mixture of polyoxyethylene-polyoxypropylene-polyoxyethylene tri-block polymers, each polymer in the mixture having an average molecular weight ranging from about 1000 to about 20000.

In certain embodiments, the aqueous compositions described herein, comprises a processing aid as defined above is present in an amount ranging from about 0.1% to about 20% by weight, such as from about 4% to about 15% by weight, and from about 5% to about 11% by weight over the total weight of aqueous compositions. In certain embodiments, the capsules shells made according to the present disclosure comprise a processing aid is present in an amount ranging from about 0.5% to about 40% by weight of the total weight of the capsule shell.

In one embodiment, the aqueous composition comprises a total amount of solids ranging from about 20% to about 50% and about 25% to about 40% by weight of the total weight of the composition.

For example, in one embodiment, bulk enteric capsule shells are manufactured with polymeric composition wherein the enteric polymer is present in an amount ranging from about 10% to about 40% by weight, e.g., from about 10% to about 30% by weight, from about 15% to about 25% by weight, and from about 15% to about 20% by weight of the total weight of the aqueous composition.

In one embodiment, the aqueous compositions described herein may comprise one or more pharmaceutically acceptable agents, food acceptable colorants, or mixtures thereof. Said agents may be selected from azo-, quinophthalone-, triphenylmethane-, xanthene- or indigoid dyes; iron oxides or hydroxides; titanium dioxide; or natural dyes and mixtures thereof. Additional examples include patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, chlorophyllin, canthaxanthin, caramel, betanin and Candurin® pearlescent pigments. Candurin® is manufactured and marketed by Merck KGaA, Darmstadt, Germany and consist of titanium dioxide and/or iron oxide—approved food and pharmaceutical colorants in many countries—and potassium aluminium silicate as color carrier. The latter is a natural, also widely approved, silicate also known under the name of "mica".

In one embodiment, the pharmaceutically acceptable agents, food acceptable colorants, or mixtures thereof are present in an amount up to about 5% by weight, e.g., from about 0 to about 2.5% by weight, and from about 0 to about 1.5% by weight of the total weight of the aqueous composition of the invention. In one embodiment, the pharmaceutically acceptable agents, food acceptable colorants, or mixtures thereof are present in an amount up to about 10% by weight in the resulting capsule shell.

In one embodiment, the aqueous compositions described herein further comprise at least one film forming aid.

In one embodiment, the "film forming aid" comprises plasticizers conventionally used in the manufacture of capsule shells, and viscosity enhancers. Examples of film forming aids that display plasticizing properties include: phtalique esters (e g dimethyl-, diethyl-, dibutyl-, diisopropyland dioctyl-phtalate); citric esters (e.g. triethyl-, tributyl-, acetyltriethyl- and acetyltributyl-citrate); phosphoric esters (e.g. triethyl-, tricresyl, triphenyl-phosphate); alkyl lactate; glycerol and glycerol esters; oils and fatty acid esters; butyl stearate; dibutyl sebacate; dibutyl tartrate; diisobutyl adipate, tributyrin; propylene glycol; polyethyleneglycol (PEG), polyoxyethylene (PEO); and mixtures thereof.

In one embodiment film forming aids that display viscosity enhancing properties or act as flocculation aids are selected from: guar gum, xanthan, carrageenans, gellan gum, carboxymethyl cellulose (CMC), alkyl celluloses, polysaccharides, and mixtures thereof.

In one embodiment, film forming aids that display both plasticizing and viscosity enhancing properties are selected from glyceryl esters (e.g. glyceryl monooleate and monolinoleate, medium chain triglycerides—i.e. $C_6$-$C_{12}$ fatty acid esters of glycerol); glycol esters (e.g. propylene glycol dicaprylocaprate and monolaurate); sorbitan monoesters (e.g. sorbitan monolaurate and monooleate); sorbitan polyoxyethylene esters (e.g. polyoxyethylene sorbitan monolaurate, monopalmitate, monostearate and monooleate); polyoxyethylene (POE) ethers (e.g. polyethylene glycol dodecyl ether); glycerol; polyethylene glycols (e.g. PEG 4000, PEG 6000); glycerol polyethylene glycol ricinoleate; linoleoyl macrogolglycerides; and mixtures thereof.

In one embodiment, film forming aids are selected from thickening agents, structuring agents, surfactants, and plasticizers, e.g., hypromellose; alkyl cellulose and other cellulosic derivatives; polyvinyl acetate derivatives (PVAP); polysaccharides; glyceryl esters; glycol esters; sorbitan monoesters; sorbitan polyoxyethylene esters; polyoxyethylene (POE) ethers; glycerol; polyethylene glycols; polyols; fatty acid esters; glycerol polyethylene, glycol ricinoleate; macrogolglycerides; SLS; triethyl citrate (TEC); acetyl triethyl citrate (ATEC); triacetine; alkyl phthalate; and mixtures thereof.

In one embodiment, film forming aids are selected from: sorbitan monoesters (e.g. sorbitan monolaurate and monooleate); sorbitan polyoxyethylene esters (e.g. polyoxyethylene sorbitan monolaurate, monopalmitate, monostearate and monooleate); polyoxyethylene (POE) ethers (e.g. polyethylene glycol dodecyl ether); glycerol; Polyvinyl acetate derivatives (PVAP), cellulosic derivative (e.g. HPMC, HPC, EC, MC, CMEC, HPMCAS, HPMCP) and mixtures thereof.

In one embodiment, film forming aids are present in the aqueous composition in an amount ranging from about 0 to about 15% by weight, such as about 0 to about 10% by weight, about 0 to about 8% by weight over the total weight of the aqueous composition.

In one embodiment, plasticizers are present in the aqueous dispersion in an amount ranging from about 6% to about 20% by weight of the total weight of the aqueous composition. In one embodiment, flocculation aids are present in the aqueous dispersion in an amount ranging from 0.1% to about 10% by weight of the total weight of the aqueous composition. The appropriate amounts of plasticizer and/or flocculation aids are dependent upon the type of polymer to be used in the aqueous composition of the present disclosure.

In one embodiment, the capsule shells of the present disclosure contain plasticizers in an amount ranging from about 10% to about 40% by weight of the total weight of the capsule shell. In one embodiment the capsule shells of the present disclosure contain plasticizers in an amount ranging from about 1% to about 30% by weight of the total weight of the capsule shell.

In one embodiment, the water is purified in a manner that is acceptable for pharmaceutical uses as defined under the United States Pharmacopeial Convention (USP) standards for purified water in USP32 and USP34-NF29. It will be understood that the aqueous composition described herein allow for non-aqueous solvents in trace amounts. Typical non-aqueous solvents are for example ethanol, or other low molecular weight alcohols conventionally used as solvents, chlorinated solvents, ethers.

In one embodiment, the aqueous compositions comprise an aqueous dispersion of non-salified controlled release polymer, wherein water is present in an amount ranging from about 50% to about 85% by weight of the total weight of said aqueous composition. In one embodiment capsule shells made according to the present disclosure contain water in an amount ranging from about 1% to about 20% by weight of the total weight of the capsule shell.

In another embodiment the aqueous compositions comprise an aqueous dispersion of non-salified controlled release polymer, being present in an amount ranging from about 10% to about 50% by weight of the total weight of said aqueous composition; at least one processing aid present in an amount ranging from about 0.1% to about 20% by weight of the total weight of said aqueous composition; water; one or more pharmaceutically acceptable agents, food acceptable colorants, or mixtures thereof; and film forming aids.

In one embodiment, the present disclosure also provides capsule shells comprising the aqueous compositions described herein, for example, as bulk enteric hard capsule shells. In one embodiment, hard capsule shells are obtainable using the aqueous compositions disclosed above and the processes as disclosed below, e.g., dip moulding.

In one embodiment, the hard capsule shells as described comprise a shell thickness (after drying to bring the water content of the shell below 6% by weight over the weight of the shell) lower than about 250 µm, e.g., at about 150 µm, and at about 70 µm. Thus, in one embodiment, the shell thickness may range from about 70 µm to about 150 µm. In one embodiment, the soft capsule shells of the present disclosure may have a shell thickness ranging from about 140 µm to about 300 µm.

In one embodiment, the shells may be externally coated with additional one or more polymer layers. Alternatively, the shells are monolayer, i.e., no external additional polymer layers are present. Thus, in one embodiment, no additional functional polymer layers are present.

Unless otherwise indicated, "functional polymer layers" means layers containing functional polymers that impart particular mechanical or chemical properties to the shell. Capsule banding or sealing are not presently considered as applying additional external layers, hence banded or sealed capsule shells and capsule are well within the scope of the present disclosure.

In one embodiment, the present disclosure provides capsule shells comprising controlled release polymer being present in an amount ranging from about 40% to about 75% by weight of the total weight of said capsule shell; at least one processing aid present in an amount ranging from about 15% to about 49% by weight of the total weight of said capsule shell, wherein said at least one processing aid is selected from polyoxyethylene-polyoxypropylene-polyoxyethylene tri-block polymers or mixtures thereof, and comprise an average molecular weight ranging from about 1000 to about 20000 and a polyoxyethylene ratio ranging from about 10% to about 80%; and water.

In one embodiment, the controlled release polymer is present in an amount ranging from about 50% to about 75% by weight over the total weight of the shell.

In one embodiment, the processing aid is present in an amount ranging between about 2% to about 40% by weight over the weight of the composition. In another embodiment, the processing aid is present in an amount ranging from about 8% to about 40% by weight over the total weight of said controlled release polymer in said composition and shell, respectively.

The shell may comprise any one of the processing aids or mixtures of processing aids as discussed above in connection with the aqueous composition. In one embodiment, the processing aid may be a plasticizer present in an amount ranging from about 8% to about 40% by weight of the total weight of the shell. In one embodiment, the processing aid may be a flocculation aid or viscosity enhancer present in an amount ranging from about 0.5% to about 20% of the total weight of the shell.

Typical amounts of water are below about 20% by weight over the total weight of the shell, such as below about 10% by weight, below about 8% by weight, and below about 6% by weight over the total weight of the shell. In one embodiment, the amount of water, as equilibrated with the relative humidity of the outside air, ranges from about 2% to about 20% by weight of the total weight of the capsule shell.

In one embodiment, the capsule shells further comprise at least one encapsulated active ingredient. Thus, the capsules may be filled with one or more acid-instable substances and/or one or more substances associated with gastric side effects in humans and/or animals.

In one embodiment, acid-instable substances are natural or synthetic substances that undergo chemical degradation or modification in the acid environment present in the stomach of a subject. In one embodiment, substances associated with gastric side effects are pharmaceutical drugs or compositions intended for human or animal oral administration, whose release in the stomach upon oral administration to a human or animal being is associated to gastric side-effects, such as gastric reflux or impairment of physiological and/or structural integrity of gastric mucosa (e.g. stomach ulcers).

In one embodiment, the at least one active ingredient comprises a solid, semi-solid, or liquid form.

In one embodiment, the shells further comprise one or more pharmaceutically or food acceptable colorants, as defined above. One or more pharmaceutically acceptable agents or food acceptable colorants are present in amounts ranging from about 0 to about 15% by weight, such as, from about 0 to about 10% by weight and from 0 to about 8% by weight over the total weight of the shells.

In one embodiment, the shells further comprise film forming aids as defined above. Film forming aids may be present in amounts ranging from about 0 to about 40% by weight, such as, from about 0 to about 30% by weight and from about 0 to about 25% by weight over the total weight of the shells.

In one embodiment, capsule shells according to the compositions and methods of the present disclosure have dissolution and disintegration profiles consistent with FIG. 1. These disintegration and dissolution profiles may be difficult to be achieved by capsule shells obtained using traditional water based solutions containing lower amounts of controlled release polymers.

The described filled capsules may be made tamper-proof by using appropriate sealing or banding techniques, or other techniques well-known to skilled artisan. It should be noted that some conventional banding and/or sealing practices use polymer solutions in water/ethanol or water/isopropanol solutions. Thus, traces of such non-aqueous solvents may be found if an elemental analysis is performed on a sealed or banded capsule without making a distinction between ingredients that are part of the shell and ingredients that are part of the band or sealing subsequently applied. Capsules made according to the compositions and methods of the present disclosure, but containing traces of solvent derived from said sealing or banding techniques are encompassed herein.

In one embodiment the present disclosure is directed to processes and methods to make capsule shells and capsules comprising the aqueous composition described herein. Despite the high solid content, the aqueous compositions described herein have low viscosity when the controlled release polymer is in a dispersed state and not in solution. The low viscosity of the aqueous solutions results in improved capsule manufacturing processes.

The viscosity of the compositions according to the present disclosure may be measured with methods and instruments known to one of skill in the art. In one embodiment, the viscosity of the aqueous compositions used for the manufacture of hard capsules described herein, when measured at 21° C. with a Brookfield viscosimeter equipped with a spindle 27 at a speed of 10 RPM, range from about 1cP to about 5000 cP, e.g., from about 500 cP to about 3000 cP, and from about 1000 cP to about 2500 cP. The spindle or rotational speeds of the viscometer may be adjusted as needed to more appropriately read the viscosity of compositions according to the present disclosure.

In one embodiment, the viscosity of the aqueous compositions used for the manufacture of soft capsules described herein, range from about 14000 cP to about 50000 cP.

In one embodiment, the aqueous compositions to be used in the context of the manufacturing processes described below are the aqueous compositions as discussed above. Accordingly, any consideration and embodiment discussed in connection with the aqueous compositions apply to the processes and methods described herein to the extent that it is technically possible.

Accordingly, in one embodiment, the present disclosure provides dip-moulding processes for the manufacture of hard capsule shells, wherein the processes comprise providing an aqueous composition comprising: an aqueous dispersion of controlled release polymer, said polymer being present in an amount ranging from about 10% to about 40% by weight of the total weight of said aqueous composition; at least one processing aid present in an amount ranging from about 0.5% to about 20% by weight of the total weight of said aqueous composition, and water; adjusting said aqueous composition to a temperature (T1) ranging from about 5° C. to a temperature below the film-forming temperature (MFFT); pre-heating moulding pins at a dipping temperature (T2) ranging from about 15° C. to about 70° C. higher than said temperature T1; dipping the pre-heated moulding pins into said aqueous composition; forming a film on said moulding pins by withdrawing said pins from said aqueous composition; and drying the film on said moulding pins to form bulk enteric hard capsule shells.

In one embodiment, the aqueous composition is kept at a temperature ranging (T1) from about 5° C. to about 40° C., such as, for example from about 15° C. to about 35° C., and from about 15° C. to about 30° C.

In one embodiment, pins are pre-heated and dipped at a temperature ranging from about 15° C. to about 70° C. higher than the temperature (T1) of the aqueous composition in the second step. For example, the temperature may range from about 15° C. to about 50° C. and from about 25° C. to about 50° C. higher than the temperature of the aqueous composition in the second step. In one embodiment, pins are pre-heated to a temperature ranging from about 45° C. to about 90° C.

In one embodiment, the pins are only dipped once. In other words, no multiple dipping of the pins is necessary to obtain a pick-up of material on pins surface sufficient to obtain a film endowed with desirable mechanical properties.

Without wanting to be bound by any theory, it is believed that the temperature T2 is high enough to induce coalescence in the aqueous composition. The temperature at which the aqueous composition coalesces can also be referred to as setting temperature, above the minimum film-forming temperature (MFFT). The setting temperature is a parameter of aqueous compositions to be used in the manufacture of hard capsules that is well known to any skilled person. Conventional methods (e.g. thermogelling dip-moulding processes known for the manufacture of hard capsule shells using cellulose derivatives like HPMC) identified the setting temperature identifies with the gelification of the composition, whereas the present disclosure relates the setting temperature to the coalescence of the composition.

In one embodiment, the pins are dried according to drying techniques typically applied in the field of hard capsules, and known to a skilled artisan. Said techniques may be accomplished using equipment known to the skilled person for this purpose. In one embodiment, drying can be performed, for example, by placing the pins in ovens. In one embodiment, of the drying step is performed at a temperature ranging from about 20° C. to about 90° C.

In one embodiment, the moulding processes further comprises filling hard capsules shells with one or more substances as disclosed above. In yet another embodiment the moulding processes further comprise making a filled hard capsule tamper-proof by sealing and/or banding the filled hard capsule manufactured according to the methods disclosed herein.

In another embodiment, the present disclosure is also directed to the methods of manufacturing soft capsules with the aqueous dispersions disclosed herein. In certain embodiments of the present disclosure the drum temperature is different to that of traditional methods. In certain embodiments, the drum is heated to a temperature ranging from about 25° C. to about 75° C.

The following non-limiting examples are offered to further clarify the present disclosure.

EXAMPLES

Test Procedures

A suitable test procedure to test disintegration properties of the shells (and capsules) is as follows: USP Apparatus basket-rack assembly consisting of six open-ended transparent tubes, each tube being provided with a disk; Disintegration media: simulated gastric fluid at pH 1.2 with NaCl for 2 h then simulated intestinal fluid at pH 6.8 with $KH_2PO_4$+ NaOH; Test conditions: fluid kept at 37° C.; oscillation frequency was 30/min; volume of dissolution medium was 800 ml; number of samples tested was 6. Test shells #0 are pre-filled with 450 mg of a mix of lactose plus 0.1% B2 (indigo blue). Capsules are placed in the tubes and a disk is over imposed. The basket is then placed in the simulated gastric fluid for 2 h and then moved to the simulated intestinal fluid.

A suitable test procedure for dissolution properties of the shells (and capsules) is as follows: USP Dissolution Apparatus 2 (paddle), dissolution media: simulated gastric fluid at pH 1.2 0.1N HCl for 2 h then simulated intestinal fluid at pH 6.8 with $Na_3PO_4$; Test conditions: fluid kept at 37° C., paddle vessel (USP/NF) of cylindrical form with spherical end; rotation speed was 50 rpm; dissolution liquid volume is 750 ml; number of samples is 6. Test shells #0 are filled with 380 mg of acetaminophen. Capsules are then placed into the vessel which is placed in the simulated gastric fluid for 2 h. Subsequently, 250 ml of 0.20M tribasic sodium phosphate are added to simulated intestinal fluid pH 6.8. UV ($\lambda$=300 nm) is used to quantify dissolved acetaminophen (as % of filled amount) in the dissolution media. Measures are made every 15 minutes when in the simulated gastric fluid and every 3 minutes in the simulated intestinal fluid.

When tested according to USP32-NF27 monographs <701> and <711> for delayed-release dosage forms, respectively, the capsule shells once filled with acetaminophen showed at least the following profiles:

Disintegration: release less than 10% of total encapsulated acetaminophen after 2 hours at pH 1.2; and Dissolution: release less than 10% of total encapsulated acetaminophen after 2 hours at pH 1.2, where 80% of the acetaminophen was released after 45 minutes at pH 6.8.

Description of the Test Protocols

Determination of the ability for the aqueous dispersion to form a continuous film: the prepared aqueous dispersion is casted on a hot (60° C.) glass plate using Capsugel film cast equipment (modified motorized Thin Layer Chromatography Plate Coater unit from CAMAG) or any other conventional drawdown coating equipment to make a uniform thin film having a dry thickness of about 100 μm. The casted film on the glass plate is kept in an oven during 1 hour at 60° C., and then stored for at least 2 hours at room temperature and 50% RH to allow full drying. Once dried, the obtained film is removed from the glass plate and evaluated for visual, physical properties, and thermal properties (including DSC and minimum film-forming temperature (MFFT) as per standard operating procedures for films and coating evaluation).

Evaluation of the aqueous dispersion setting properties: to reproduce the capsule dipping process, a simplified lab-scale equipment called Pin Lab Dipper has been developed to mimic the dipping of a pin into the solution. This device is equipped with an electronically-assisted module to control the pin dipping profile and withdrawal profile. It also ensures the pin rotation to the upright position and regulates the pin temperature. The dipping step is followed by a drying sequence with appropriate hot air. This test evaluates the potential setting properties of the tested solutions, whether it is possible to form a continuous and homogeneous film on the stainless steel pin by dip moulding processes.

Setting conditions for Example 1 below: dipping dish container at 21° C., pre-heated pin at 70° C., drying temperature 60° C. at room relative humidity. Visual control of capsule shell for possible defect, weight and thickness measurement (top wall, side wall and/or shoulder).

Evaluation of the film-formation ability of the composition: bench pick-up (BPU) test allows evaluating film formation ability of the formulation upon dipping a heated pin in the formulation. Pins are heated at a desired temperature in an oven and then dipped inside the formulation which is at a given temperature. Pick-up and setting properties are evaluated. Pins are then allowed to dry in an oven at the desired temperature and dry film is observed.

Example 1

In a reactor of 300 mL, 60 g of Poloxamer (Lutrol L44 from BASF) are mixed with 140 mL of purified water under gentle stirring for 30 min. The obtained solution is poured in a 2-liter reactor containing 1000 g of Aquacoat CPD 30 dispersion from FMC at room temperature and stirred overnight for 12 hours for complete homogenization at 21° C. Usually, the viscosity of the formulation increases slightly from milk to liquid cream during this maturation step. A film and a capsule shell are prepared from this dispersion and evaluated according to the protocols described above.

Example 2

In a reactor of 200 mL, 45 g of Poloxamer 124 (Lutrol L44) are mixed with 105 mL of purified water under gentle stirring for 30 min. The obtained solution is poured in a 2-liter reactor containing 1000 g of Aquacoat CPD 30 dispersion at room temperature and stirred overnight for 12 hours for complete homogenization at 21° C. (Example 2). A film and a capsule shell are prepared from this dispersion and evaluated according to the protocols described above.

Example 3

In a reactor of 150 mL, 30 g of Poloxamer 124 (Lutrol L44) are mixed with 70 mL of purified water under gentle stirring for 30 min. The obtained solution is poured in a 2-liter reactor containing 1000 g of Aquacoat CPD 30 dispersion at room temperature and stirred overnight for 12 hours for complete homogenization at 21° C. (Example 3). A film and a capsule shell are prepared from this dispersion and evaluated according to the protocols described above.

Results:

TABLE 1

| Example # | Commercial name | poloxamer/CAP ratio | film | viscosity (cP) (3) | Young modulus MPa (2) | Elongation at break % (2) | MFFT (° C.) | Tg (° C.) | capsule shell (1) |
|---|---|---|---|---|---|---|---|---|---|
| 1 | Lutrol L44 | 1/5 | uniform film | 1300 | 720 | 40 | 30 | 47 | adequate pick-up |
| 2 | Lutrol L44 | 3/20 | uniform film | 800 | 860 | 30 | 30 | 46 | satisfying pick-up |
| 3 | Lutrol L44 | 1/10 | cracked film | 21 | N/A | N/A | 30 | 45 | no pick up |

(1) pick up: formation of a continuous & homogeneous film of about 100 μm +/− 20 μm on the stainless steel pin
(2) film stored at 23% RH, measured with Instron 4443, 4 × 0.5 inches tensile specimens
(3) measured with Brookfield, spindle 27, 10 RPM, 21° C.

Examples 4-10

The aqueous dispersions of Examples 4-10 have been prepared to compare various grades of poloxamer (Pluronic from BASF) according to the protocol described for Example 1, with respectively Pluronic F108, Pluronic F127, Pluronic F68, Pluronic F87, Pluronic L35, Pluronic L43, Pluronic L62 instead of Lutrol L44 in the same proportions: 1/5 (w/w) poloxamer (30% solution)/CAP (30% dispersion) ratio. A film and a capsule shell are prepared from this dispersion and evaluated according to the protocols described above.

Results:

Example 11

In a reactor of 300 mL, 60 g of Poloxamer 124 (Lutrol L44) are mixed with 140 ml of purified water under gentle stirring for 30 min. The obtained solution is poured in a 2-liter reactor containing 1000 g of Aquacoat CPD 30 dispersion and 600 g of a HPMC 20% solution at room temperature and stirred overnight for 12 hours for complete homogenization at 21° C. A film and a capsule shell are prepared from this dispersion and evaluated according to the protocols described above.

Example 12

In a reactor of 300 mL, 60 g of Poloxamer 124 (Lutrol L44) are mixed with 140 mL of purified water under gentle stirring for 30 min. The obtained solution is poured in a 2-liter reactor containing 1000 g of Aquacoat CPD 30 dispersion at room temperature and stirred overnight for 12 hours for complete homogenization at 21° C. After maturation, a titanium dioxide slurry is added to the obtained dispersion under gentle stirring until complete homogenization at 21° C., at a ratio of 5/95 (w/w slurry/dispersion). The titanium dioxide slurry comprises 21.8% of $TiO_2$, 19.4% of a 20% HPMC solution, 58.1% of water pH 4 and 0.7% of a cationic compound such as chitosan. The chitosan is first pre-dispersed in the water pH 4 and the solution is defoamed overnight. $TiO_2$ is then added and dispersed 3×2 min at Vmax with a high speed homogenizer such as Ultra-Turrax. Then the HPMC solution is added and stirred 3 min at 1200 RPM with a high speed homogenizer. In addition, 0.2% of pigment Patented Blue dispersed in a minimum of water is optionally incorporated to the final preparation under gentle stirring to obtain an opaque blue film and capsule shell. A

TABLE 2

| Example # | Commercial name | Poloxamer grade (2) | Mw (2) | EO % (2) | HLB (2) | Observation |
|---|---|---|---|---|---|---|
| 4 | Pluronic F108 | 338 | 16500 | 80 | >24 | no pick up (1) |
| 5 | Pluronic F127 | 407 | 13333 | 70 | >24 | no pick up (1) |
| 6 | Pluronic F68 | 188 | 9000 | 80 | >24 | no pick up (1) |
| 7 | Pluronic F87 | 237 | 7666 | 70 | >24 | no pick up (1) |
| 8 | Pluronic L35 | N/A | 1900 | 50 | 18-23 | weak thin film formed |
| 1 | Lutrol L44 | 124 | 2000-2200 | 40 | 12-18 | adequate film formed |
| 9 | Pluronic L43 | N/A | 1850 | 30 | 7-12 | weak thick film formed |
| 10 | Pluronic L62 | 182 | 2450 | 20 | 1-7 | poor thick film formed |

(1) pick up: formation of a continuous & homogeneous layer/film on the stainless steel pin
(2) data according to BASF technical datasheets film and a capsule shell are prepared from this dispersion and evaluated according to the protocols described above.

Example 13

In a reactor of 200 mL, 45 g of Poloxamer 124 (Lutrol L44 from BASF) are mixed with 105 ml of purified water under gentle stirring for 30 min. In a separate beaker of 100 mL, 3 g of carboxymethyl cellulose (Blanose 7MF-PH from Ashland) are added to 72 mL of purified water under high speed homogenization, using for example an Ultra-Turrax homogenizer during 20 min before a 30 min-defoaming step under vacuum. Both obtained Poloxamer and Blanose solutions are poured in a 2-liter reactor containing 1000 g of Aquacoat CPD 30 dispersion at room temperature and stirred overnight for 12 hours for complete homogenization at 21° C. A film and a capsule shell are prepared from this dispersion and evaluated according to the protocols described above under a) & b).

Example 14

In a reactor of 300 mL, 60 g of polyoxyethylene (Polyox N10 from Dow) are mixed with 140 mL of purified water under gentle stirring (150 RPM) at 80° C. during one night. The obtained solution is then cooled down at room temperature and poured in a 2-liter reactor containing 1000 g of Aquacoat CPD 30 dispersion comprising 23% of non-salified CAP and about 7% of Poloxamer; the mixture is stirred during one night at 200 RPM for complete homogenization at 21° C. A film and a capsule shell are prepared from this dispersion and evaluated according to the protocols described above.

Example 15

In a reactor of 300 mL, 1.4 g of carrageenan (Satiagum UTC 10 grade lambda from Cargill) is mixed with 140 mL of purified water under gentle stirring for 30 min. Then 60 g of Poloxamer 124 (Lutrol L44) is added to this solution under gentle stirring for 30 min. The obtained solution is poured in a 2-liter reactor containing 1000 g of Aquacoat CPD 30 dispersion at room temperature and stirred overnight for 12 hours for complete homogenization at 21° C. A film and a capsule shell are prepared from this dispersion and evaluated according to the protocols described above.

Results:

TABLE 3

| Example # | film | viscosity (cP) (3) | Young modulus (MPa) (2) | Elongation at break % (2) | capsule shell (1) |
|---|---|---|---|---|---|
| 11 | uniform film | >2000 | 867 | 29 | adequate pick-up |
| 12 | uniform thick film | N/A | 515 | 45 | adequate opaque pick-up (optionnally blue) |
| 13 | uniform slightly bitty film | 1762 | 740 | 41 | satisfying pick-up |
| 14 | thick film | N/A | 669 | 12 | adequate pick-up |
| 15 | uniform transparent film | 1987 | 614 | 48 | adequate pick-up |

(1) pick up: formation of a continuous & homogeneous film on the stainless steel pin
(2) film stored at 23% RH, measured with Instron 4443, 4 × 0.5 inches tensile specimens
(3) measured with Brookfield, spindle 27, 10 RPM, 21° C.

Examples 16-18

Evaluation of various process conditions on PLD—Dispersion temperature: An aqueous dispersion of CAP and Poloxamer is prepared according to the Example 1. It is then poured into the dipping dish container of the electronically-assisted Pin Lab Dipper, in which a robotized hot pin at 70° C. is dipped and withdrawn according to a pre-established sequence before drying at 60° C. The dipping dish container temperature is respectively set at 14° C., 18° C. and 24° C. for Examples 16, 17 and 18.

Examples 19 and 20

Evaluation of various process conditions on PLD—Pin temperature: An aqueous dispersion of CAP and Poloxamer is prepared according to the example 1. It is then poured into the dipping dish container at 21° C. of the electronically-assisted Pin Lab Dipper, in which a robotized hot pin is dipped and withdrawn according to a pre-established sequence before drying at 60° C. The pin temperature is respectively set at 67° C. and 73° C. for the example 19 and 20.

Results

TABLE 4

| Example # | dish T° C. | pin T° C. | body* weight (g) | side wall* thickness (μm) | top wall* thickness (μm) | shoulder* thickness (μm) | viscosity (cP) (1) | Observation |
|---|---|---|---|---|---|---|---|---|
| 1 | 21 | 70 | 60 | 100 | 125 | 80 | 1350 | adequate pick-up |
| 16 | 14 | 70 | <40 | <60 | broken | broken | <800 | no pick up |
| 17 | 18 | 70 | 44 | 80 | 90 | 50 | 1150 | thin film |
| 18 | 24 | 70 | 68 | 120 | 150 | 85 | 1550 | thick film |
| 19 | 21 | 67 | 50 | 95 | 85 | 60 | 1350 | thin film |
| 20 | 21 | 73 | 60 | 110 | 125 | 80 | 1350 | slightly thick film |

*average data
(1) measured with Brookfield, spindle 27, 10 RPM, 21° C.

Example 21

Evaluation of the aqueous dispersions on pilot capsule machine: In a reactor of 1 L, 240 g of Poloxamer (Lutrol L44 from BASF) are mixed with 560 ml of purified water under gentle stirring for 30 min. The obtained solution is poured in a 5-liter reactor containing 4000 g of Aquacoat CPD 30 dispersion at room temperature and stirred overnight for 12 hours for complete homogenization at 21° C. Usually, the viscosity of the formulation increases slightly from milk to liquid cream during this maturation step.

Manufacture of the capsules with pilot machine: The defined aqueous dispersion is transferred into the dipping dish of a pilot machine of conventional hard capsule production equipment. While keeping the dipping solution at 21° C., hot stainless steel pins size 0 at 70° C. (pins body or cap are pre-heated at 70° C. in the corresponding section of the pilot machine) are dipped into the aqueous dispersion according to a well defined dipping profile in an attempt to manufacture capsules (body or cap) with the same dimension specifications to the conventional hard capsules. After withdrawal the dipped pins are transferred to a drying section where they are submitted to hot air at defined speed, temperature and humidity. When dry, the body or cap capsules parts obtained are stripped of the pins, cut and assembled for visual control and physical property measurements, including weight, dimensional evaluation, and dissolution/disintegration tests.

Examples 22 and 23

The aqueous dispersion is prepared according to the Example 21. It is then transferred into the dipping dish of a pilot machine of conventional hard capsule production equipment, to manufacture capsules following the same protocol as described for Example 21. The hot stainless steel pins are heated at 70° C. The dipping solution and the dipping dish container are kept at 19° C. and 23° C. for the respective Example 22 and 23.

Examples 24 and 25

The aqueous dispersion is prepared according to the Example 21. It is then transferred into the dipping dish of a pilot machine of conventional hard capsule production equipment, to manufacture capsules following the same protocol as described for example 21. The dipping solution and the dipping dish container are kept at 21° C. The hot stainless steel pins are respectively heated at 60° C. and 65° C. for the Examples 24 and 25.

Example 26

In a reactor of 1 L, 240 g of Poloxamer 124 (Lutrol L44) are mixed with 560 ml of purified water under gentle stirring for 30 min. The obtained solution is poured in a 5-liter reactor containing 4000 g of Aquacoat CPD 30 dispersion at room temperature and stirred overnight for 12 hours for complete homogenization at 21° C. After maturation, a titanium dioxide slurry is added to the obtained dispersion under gentle stirring until complete homogenization at 21° C., at a ratio of 5/95 (w/w slurry/dispersion). The titanium dioxide slurry comprises 21.8% of $TiO_2$, 19.4% of a 20% HPMC solution, 58.1% of water pH 4 and 0.7% of a cationic compound such as chitosan. The chitosan is first pre-dispersed in the water pH 4 and the solution is defoamed overnight. $TiO_2$ is then added and dispersed 3×2 min at Vmax with a high speed homogenizer such as Ultra-Turrax. Then the HPMC solution is added and stirred 3 min at 1200 RPM with a high speed homogenizer. In addition, 0.25% of pigment yellow 6 dispersed in a minimum of water is optionally incorporated to the final preparation under gentle stirring at 21° C. to obtain an opaque orange capsule shell.

The defined aqueous dispersion is transferred into the dipping dish of a pilot machine of conventional hard capsule production equipment. While keeping the dipping solution at 21° C., hot stainless steel pins size 0 at 70° C. (pins body or cap are pre-heated at 70° C. in the corresponding section of the pilot machine) are dipped into the aqueous dispersion according to a well defined dipping profile in an attempt to manufacture capsules (body or cap) with the same dimension specifications to the conventional hard capsules. After withdrawal the dipped pins are transferred to a drying section where they are submitted to hot air at defined speed, temperature and humidity. When dry, the body or cap capsules parts obtained are stripped of the pins, cut and assembled for visual control and physical property measurements, including weight, dimensional evaluation, and dissolution/disintegration tests.

Example 27

In a reactor of 1 L, 240 g of Poloxamer 124 (Lutrol® L44) are mixed with 560 mL of purified water under gentle stirring for 30 min. The obtained solution is poured in a 5-liter reactor containing 4000 g of Aquacoat CPD 30 dispersion and 2400 g of a HPMC 20% solution at room temperature and stirred overnight for 12 hours for complete homogenization at 21° C.

The defined aqueous dispersion is transferred into the dipping dish of a pilot machine of conventional hard capsule production equipment. While keeping the dipping solution at 21° C., hot stainless steel pins size 0 at 70° C. (pins body or cap are pre-heated at 70° C. in the corresponding section of the pilot machine) are dipped into the aqueous dispersion according to a well defined dipping profile in an attempt to manufacture capsules (body or cap) with the same dimension specifications to the conventional hard capsules. After withdrawal the dipped pins are transferred to a drying section where they are submitted to hot air at defined speed, temperature and humidity. When dry, the body or cap capsules parts obtained are stripped of the pins, cut and assembled for visual control and physical property measurements, including weight, dimensional evaluation, and dissolution/disintegration tests.

Results:

TABLE 5

| Example # | dish T° C. | pin T° C. | body* weight (g) | side wall* thickness (μm) | top wall* thickness (μm) | shoulder* thickness (μm) | viscosity (cP) | Observation defects |
| --- | --- | --- | --- | --- | --- | --- | --- | --- |
| 21 | 21 | 70 | 62 | 107 | 124 | 88-144 | 127 (1) | adequate capsule |
| 22 | 19 | 70 | 56 | N/A | 183 | N/A | 137 (1) | many visual defects |
| 23 | 23 | 70 | 67 | N/A | 198 | N/A | 194 (1) | many visual defects |

TABLE 5-continued

| Example # | dish T° C. | pin T° C. | body* weight (g) | side wall* thickness (μm) | top wall* thickness (μm) | shoulder* thickness (μm) | viscosity (cP) | Observation defects |
|---|---|---|---|---|---|---|---|---|
| 24 | 21 | 60 | 53 | N/A | 95 | N/A | 213 (2) | thin capsule |
| 25 | 21 | 65 | 58 | N/A | 152 | N/A | 182 (2) | adequate capsule |
| 26 | 21 | 70 | 63 | 110 | 190 | 89 | 180 (1) | adequate white capsule (optionally orange) |
| 27 | 21 | 70 | 60 | 109 | 117 | 85 | 530 (1) | adequate harder capsule |

*average data for selected defined dipping profile
Viscosity measured with Capsugel pilot machine viscosimeter; speed (1) v = 3 (2) v = 5

Dissolution Profile of a Capsule Shell Containing Acetaminophen. UV-Titration (300 nm)

TABLE 6

| | | time (min) | | | | | | | | |
|---|---|---|---|---|---|---|---|---|---|---|
| | | 0 | 15 | 30 | 45 | 60 | 75 | 90 | 105 | 120 | 123 |
| Example 21 | % dissolved | 0.00 | 0.10 | 0.30 | 0.55 | 0.80 | 1.02 | 1.25 | 1.45 | 1.62 | 2.88 |
| Example 26 | % dissolved | 0.00 | 0.07 | 0.35 | 0.66 | 0.98 | 1.32 | 1.62 | 1.90 | 2.16 | 3.79 |

| | | time (min) | | | | | | | | |
|---|---|---|---|---|---|---|---|---|---|---|
| | | 126 | 129 | 132 | 135 | 140 | 145 | 150 | 155 | 170 | 185 |
| Example 21 | % dissolved | 8.44 | 20.23 | 34.58 | 47.75 | 65.30 | 77.54 | 85.55 | 97.74 | 99.36 | 100.00 |
| Example 26 | % dissolved | 6.10 | 14.97 | 32.97 | 50.90 | 71.71 | 84.28 | 91.17 | 99.04 | 98.98 | 99.11 |

Example 28

A dispersion at 30% of poloxamer 144 (Pluronic L44, BASF) is prepared: 70 g of demi water is heated at 80° C., 30 g flakes of poloxamer are dispersed and vigorously stirred until complete dissolution. Solution is allowed to cool back to room temperature under moderate stirring (350 rpm). 100 g of CAP dispersion in water (30% solids, Aquacoat CPD-30, FMC) is filtered on 250 μm sieve and moderately stirred at 350 rpm. 10 g of poloxamer solution is added drop wise under moderate stirring within 10 minutes. Additional stirring occurs during 30 minutes.

The dispersion obtained is poured in vessel where the dip-molding will take place. Pins are heated to 50° C. for 1 hour to let them stabilize with surroundings and lubricated with demolding agent. The heated pin is dipped into dispersion at room temperature and withdrawn with accurate speed to adjust the profile of film and the quantity of material picked up. The film is dried on pin at 50° C. for 15 minutes, stripped off, cut at the adequate length depending on the part manufactured. When cap and body are manufactured, two pieces capsule is assembled. Thickness of film is measured on top, on shoulders and on side and compared to technical reference file of hard gelatin capsules. The thickness targeted is about 100 μm. The obtained capsules are filled with APAP, closed and sealed with ethanol/water mixture. A film and capsule shell are prepared from this dispersion and evaluated according to the dissolution protocol described above.

Examples 29 and 30

The same protocol as in Example 28 is applied to compositions where Poloxamer 144 is replaced by PEG6000, and Polyox N10 (100,000 g/mol) respectively. Film and capsule shells are prepared from these dispersions and evaluated according to the dissolution protocol described above.

Example 31

A dispersion of 100 g of HPMCAS (Aquoat, Shin Etsu) is prepared according to Shin-Etsu protocol to achieve a dispersion with 14% solids. 20% TEC is added drop-wise to the dispersion and stirred for 2 hours at room temperature before use. When pin is heated to 50° C. it is dipped into the vessel, the polymer aggregates but the film rapidly collapses and flows down.

Example 32

100 g of polyvinylacetatephtalate dispersion provided by Colorcon (Opadry) is prepared according to supplier protocol, in order to achieve a dispersion with 14% solids, 20% TEC is added dropwise to the dispersion and stirred for 2 hours at room.

Example 33

In a beaker of 400 ml, 60 g of Aquacoat CPD 30 were placed at 150 rpm magnetic stirring at room temperature; 3.37 g of P124 were added at 150 rpm stirring at room temperature. Two hours later, 4.20 g of titanium dioxide slurry were added at 150 rpm magnetic stirring at room temperature. Titanium dioxide slurry comprised 56.85 wt % water pH 4, 21.75% TiO2, 2.0 wt % Eudragit E PO and 19.4 wt % of a 20% HPMC solution. The TiO2 and Eudragit E PO were first pre-dispersed in water pH 4 and let under magnetic stirring at 700 rpm for at least 30 minutes. Dispersion 3×2 minutes at 13 000 rpm with a high speed homogenizer was then performed. The 20% HPMC solution was added and stirred 3 minutes at 1200 rpm (magnetic stirrer). Formulation was allowed to maturate overnight at room temperature, at 80 rpm magnetic stirring.

Example 34

In a beaker of 400 ml, 60 g of Aquacoat CPD 30 were placed at 150 rpm magnetic stirring at room temperature;

16.05 g of P124 were added at 150 rpm stirring at room temperature. Two hours later, 6.70 g of titanium dioxide slurry were added at 150 rpm magnetic stirring at room temperature. Titanium dioxide slurry comprised 56.85 wt % water pH 4, 21.75% TiO2, 2.00 wt % Eudragit E PO and 19.40 wt % of a 20% HPMC solution. The TiO2 and Eudragit E PO were first pre-dispersed in water pH 4 and let under magnetic stirring at 700 rpm for at least 30 minutes. Dispersion 3×2 minutes at 13 000 rpm with a high speed homogenizer was then performed. The 20% HPMC solution was added and stirred 3 minutes at 1200 rpm (magnetic stirrer). Formulation was allowed to maturate overnight at room temperature, at 80 rpm magnetic stirring.

Results

BPU test conditions: pin temperature: 60° C.; formulation temperature: 28° C., heated one hour before BPU test; drying 30 minutes at 60° C. in an oven.

TABLE 7

| | BPU test | |
|---|---|---|
| Example | Pick-up and setting properties | Capsule film |
| 33 | Good pick-up and good setting | White non-brittle film |
| 34 | Medium pick-up and medium setting | White film containing grains; water exudation on pins |

Example 35

In a beaker of 400 ml, 60 g of Aquacoat CPD 30 were placed at 150 rpm magnetic stirring at room temperature; 9 g of a 20% HPMC solution were added at 150 rpm stirring at room temperature. Two hours later, 1.80 g of P124 was added at 150 rpm stirring at room temperature. Two hours later, magnetic stirring was decreased to 80 rpm for maturation overnight at room temperature.

Example 36

In a beaker of 400 ml, 60 g of Aquacoat CPD 30 were placed at 150 rpm magnetic stirring at room temperature; 0.95 ml of calcium acetate solution at 1.8 mol/l was then added. After 30 minutes, 9 g of a 20% HPMC solution were added at 150 rpm stirring at room temperature. Two hours later, 1.80 g of P124 was added at 150 rpm stirring at room temperature. Two hours later, magnetic stirring was decreased to 80 rpm for maturation overnight at room temperature.

Example 37

In a beaker of 50 ml, 9 g of P124 were introduced in 21 g of demi-water at 200 rpm magnetic stirring to obtain at 30% solution. In a beaker of 400 ml, 120 g of Aquacoat CPD 30 were placed at 150 rpm magnetic stirring at room temperature; 1.90 ml of calcium acetate solution at 1.8 mol/l was then added. After 30 minutes, 18 g of a 20% HPMC solution were added at 150 rpm stirring at room temperature. Two hours later, 12 g of P124 30% solution were added at 150 rpm stirring at room temperature. Two hours later, magnetic stirring was decreased to 80 rpm for maturation overnight at room temperature.

Results

BPU test conditions: pin temperature: 60° C.; formulation temperature: 28° C., heated one hour before BPU test; drying 30 minutes at 60° C. in an oven.

TABLE 8

| | BPU test * | |
|---|---|---|
| Example | Pick-up and setting properties | Capsule film |
| 35 | Good pick-up and good setting | Transpwerent film |
| 36 | Medium pick-up and medium setting | Transpwerent thin film |
| 37 | Good pick-up and good setting | Transpwerent thin film |

Example 38

In a beaker of 400 ml, 60 g of Aquacoat CPD 30 were placed at 150 rpm magnetic stirring at room temperature. After 30 minutes, 1.80 g of P124 were added at 150 rpm stirring at room temperature. Two hours later, 8.67 g of HPMCAS slurry were added. HPMCAS slurry comprised 78.42% of water pH4, 20.76% HPMCAS and 0.82% Eudragit E PO. HPMCAS and Eudragit E PO were mixed and then pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 400 rpm until use. Two hours after HPMCAS slurry addition in formulation, magnetic stirring was decrease to 80 rpm for maturation overnight at room temperature.

Results

TABLE 9

| Example | Film | Viscosity (Brookfield) |
|---|---|---|
| 38 | Transparent film | 3222 cP at 21° C. (S27, 6 rpm) |

Example 39

In a 1 l-beaker, 500 g of Aquacoat CPD 30 were placed at 190 rpm stirring (anchor stirrer) for 30 minutes. 15 g of P124 were then added and the whole was let at 190 rpm stirring for 2 hours. Then, 75.55 g of HPMCAS slurry were added. HPMCAS slurry comprised 74.99% of water pH4, 19.85% HPMCAS, 0.79% Eudragit E PO and 4.37% of a 20% HPMC solution. HPMCAS and Eudragit E PO were mixed and then pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 400 rpm for 30 minutes. The 20% HPMC solution was added and mixed with magnetic stirrer at 1200 rpm for 3 minutes. Slurry was kept under stirring at 400 rpm until use. Two hours after HPMCAS slurry addition in the formulation, magnetic stirring was decreased to 80 rpm for maturation overnight at room temperature.

Results

TABLE 10

| Example | Film | Viscosity (Brookfield)) | MFFT (° C.) |
|---|---|---|---|
| 39 | Transparent film | 1150 cP at 21° C. (S27, 10 rpm) | 21.8 |

Evaluation of various process conditions on PLD. A formulation was prepared according to example 39 and poured into the dipping dish container of the electronically-assisted Pin Lab Dipper, in which a robotized hot pin was dipped and withdrawn according to a pre-established sequence before drying at 60° C. Parameters were detailed in the following table.

Results

TABLE 11

| Example | Dish T° C. | Pin T° C. | Body weight* (mg) | Side wall thickness* (μm) | Top wall* (μm) | Shoulder thickness* (μm) | Observation |
|---------|------------|-----------|-------------------|---------------------------|----------------|--------------------------|-------------|
| 39 | 25 | 62 (for body) | 60.8 | 95-117 | 151 | NA | Good pick-up, good setting |

*average data for selected data

Example 40

In a 5 l-reactor maintained at 21° C., 4500 g of Aquacoat CPD 30 were placed at 190 rpm stirring (anchor paddle) for 2 hours. 135 g of P124 were then added and the whole was let at 190 rpm stirring for 2 hours. Then, 613.14 g HPMCAS dispersion were added. HPMCAS dispersion comprised 76.7% demi-water, 1.3 wt % Tween 80 and 22% HPMCAS. Demi-water was placed at 200 rpm double-stirring (three-blade propeller and magnetic stirrer) and Tween 80 was added. HPMCAS was added in demi-water containing Tween 80 during 60 minutes. HPMCAS dispersion was kept under stirring at 200 rpm for at least 30 minutes before use. Two hours after HPMCAS dispersion addition, magnetic stirring was decreased to 80 rpm for maturation overnight at room temperature.

Example 41

Same formulation than for example 40 was prepared. Titanium dioxide slurry was added to obtain white opaque capsules. 165.84 g of titanium dioxide slurry was added to 4075 g of formulation from example E6 and mixed with a spatula. Titanium dioxide slurry comprised 42.7% water pH4, 16.3% $TiO_2$, 1.5% Eudragit E PO, 14.5% of a 20% HPMC solution, 25.0% demi-water. $TiO_2$ and Eudragit E PO were mixed and added in water pH 4 at a stirring speed of 700 rpm with a deflocculator. Dispersion 3×2 minutes at 16 000 rpm with a high speed homogenizer such an ultra-turrax was then performed. Bubbles were removed by keeping the slurry under stirring for at least 30 minutes. The 20% HPMC solution was added and mixed with a spatula. Slurry was kept at 200 rpm magnetic stirring until use. Once titanium dioxide slurry was added in formulation, stirring was allowed for 45 minutes at 70 rpm, and then stirring was decreased to 50 rpm for maturation overnight at 21° C.

Example 42

In a 5 l-reactor maintained at 21° C., 4500 g of Aquacoat CPD 30 were placed at 190 rpm stirring (anchor stirrer) for 1 hour. 135 g of P124 were then added and the whole was let at 190 rpm stirring for 2 hours. Then, 680 g of HPMCAS slurry were added. HPMCAS slurry comprised 74.99% of water pH4, 19.85% HPMCAS, 0.79% Eudragit E PO and 4.37% of a 20% HPMC solution. HPMCAS and Eudragit E PO were mixed and then pre-dispersed in water pH 4 at 700 rpm stirring with a three-blade propeller and let in these conditions for at least 30 minutes. Dispersion 3×2 minutes at 13 000 rpm with a high speed homogenizer was then performed. The slurry was allowed to defoam under stirring at 400 rpm for 30 minutes. The 20% HPMC solution was added and mixed with Silverson at 1200 rpm for 3 minutes. Slurry was kept under stirring at 400 rpm until use. Two hours after HPMCAS slurry addition, magnetic stirring was decrease to 70 rpm for maturation overnight at 21° C.

The aqueous dispersions from examples 40 and 41 were transferred into the dipping dish of a pilot machine of conventional hard capsule production equipment (NMD), to manufacture capsules as previously disclosed. Dish temperature and pin temperature were given in result table.

Results

TABLE 12

| Example | Dish T° C. | Pin T° C. | Body weight* (mg) | Side wall thickness* (μm) | Top wall* (μm) | Shoulder thickness* (μm) | Viscosity (Brookfield) |
|---------|------------|-----------|-------------------|---------------------------|----------------|--------------------------|------------------------|
| 40 | 25.1 | 65 | NA | NA | NA | NA | 865 cP at 21° C. (S27, 10 rpm) |
| 41 | 23 | 62 | 70.5 | 125 | 89.2 | 65.3-79.2 | 2147 cP at 21° C. (S27, 10 rpm) |

*average data for selected defined data

Example 43

In a 2 l-reactor maintained at 21° C., 500 g of Aquacoat CPD 30 were placed at 190 rpm stirring (anchor paddle). 15 g of TEC were then added and the whole was let at 190 rpm stirring for 2 hours. Then, 72.25 g of HPMCAS slurry were added. HPMCAS slurry comprised 78.42% of water pH4, 20.76% HPMCAS and 0.82% Eudragit E PO. HPMCAS and Eudragit E PO were mixed and pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 250-300 rpm for at least one hour. Two hours after HPMCAS slurry addition in formulation, magnetic stirring was decrease to 80 rpm for maturation overnight at room temperature.

Example 44

In a 2 l-reactor maintained at 21° C., 500 g of Aquacoat CPD 30 were placed at 190 rpm stirring (anchor paddle). 7.5 g of TEC were then added and the whole was let at 190 rpm stirring for 2 hours. Then, 72.25 g of HPMCAS slurry were added. HPMCAS slurry comprised 78.42% of water pH4, 20.76% HPMCAS and 0.82% Eudragit E PO. HPMCAS and Eudragit E PO were mixed and pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 250-300 rpm for at least one hour. Two hours after HPMCAS slurry addition in formulation, magnetic stirring was decrease to 80 rpm for maturation overnight at room temperature.

Example 45

In a 2 l-reactor maintained at 21° C., 500 g of Aquacoat CPD 30 were placed at 190 rpm stirring (anchor paddle). 1.5 g of TEC was then added and the whole was let at 190 rpm stirring for 2 hours. Then, 72.25 g of HPMCAS slurry were added. HPMCAS slurry comprised 78.42% of water pH4, 20.76% HPMCAS and 0.82% Eudragit E PO. HPMCAS and Eudragit E PO were mixed and pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 250-300 rpm for at least one hour. Two hours after HPMCAS slurry addition in formulation, magnetic stirring was decrease to 80 rpm for maturation overnight at room temperature.

Results

TABLE 13

| Example | Film | Viscosity (Brookfield) | MFFT (° C.) | Pick-up and setting properties | Capsule film |
|---|---|---|---|---|---|
| 43 | Transparent film with some grains | 4341 cP at 21° C. (S27, 5 rpm) | 20.1 | NA | NA |
| 44 | Transparent film | 3824 cP at 21° C. (S27, 5 rpm) | 23.5 | Good pick-up and good setting | Transparent film |
| 45 | Transparent film | 2006 cP at 21° C. (S27, 10 rpm) | 29.2 | Good pick-up and good setting | Transparent film |

* BPU test conditions: pin temperature: 60° C.; formulation temperature: 21° C., drying 30 minutes at 60° C. in an oven.

Evaluation of various process conditions on PLD. Formulation prepared according to example 44 was poured into the dipping dish container of the electronically-assisted Pin Lab Dipper, in which a robotized hot pin was dipped and withdrawn according to a pre-established sequence before drying at 60° C. Parameters were detailed in the following table.

TABLE 14

| Example | Dish T° C. | Pin T° C. | Body weight* (mg) | Side wall thickness* (μm) | Top wall* (μm) | Shoulder thickness* (μm) | Observation |
|---|---|---|---|---|---|---|---|
| 44 | 21 | 53 (for body) | 60.5 | 112-136 | 116 | 71-86 | Good pick-up and good setting, nice capsule shell |

*average data for selected data.

Example 46

In a 2 l-reactor maintained at 21° C., 500 g of Aquacoat CPD 30 were placed at 190 rpm stirring (anchor paddle). 1.5 g of ATEC was then added and the whole was let at 190 rpm stirring for 2 hours. Then, 72.25 g of HPMCAS slurry were added. HPMCAS slurry comprised 78.42% of water pH4, 20.76% HPMCAS and 0.82% Eudragit E PO. HPMCAS and Eudragit E PO were mixed and pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 250-300 rpm for at least one hour. Two hours after HPMCAS slurry addition in formulation, magnetic stirring was decrease to 80 rpm for maturation overnight at room temperature.

Example 47

In a 2 l-reactor maintained at 21° C., 500 g of Aquacoat CPD 30 were placed at 190 rpm stirring (anchor paddle). 7.5 g of ATEC were then added and the whole was let at 190 rpm stirring for 2 hours. Then, 72.25 g of HPMCAS slurry were added. HPMCAS slurry comprised 78.42% of water pH4, 20.76% HPMCAS and 0.82% Eudragit E PO. HPMCAS and Eudragit E PO were mixed and pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 250-300 rpm for at least one hour. Two hours after HPMCAS slurry addition in formulation, magnetic stirring was decrease to 80 rpm for maturation overnight at room temperature.

Results

BPU test conditions: pin temperature: 60° C.; formulation temperature: 21° C., drying 30 minutes at 60° C. in an oven.

TABLE 15

| Example | Film | Viscosity (Brookfield) | BPU test Pick-up and setting properties | Capsule film |
|---|---|---|---|---|
| 46 | Transparent film | 3707 cP at 21° C. (S27, 5 rpm) | Slight over pick-up, good setting | Transparent film |
| 47 | Transparent film | 2053 cP at 21° C. (S27, 10 rpm) | Good pick-up good setting | Transparent film |

Example 48

In a beaker of 400 ml, 60 g of Aquacoat CPD 30 were placed at 150 rpm magnetic stirring at room temperature. After 30 minutes, 1.40 g of ATBC were added at 150 rpm at room temperature. Two hours later, 8.67 g of HPMCAS slurry were added. HPMCAS slurry comprised 78.43% of water pH4, 16.15% HPMCAS, 0.81% Eudragit E PO and 4.61% of a 20% HPMC solution. HPMCAS and Eudragit E PO were mixed and pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 400 rpm for 30 minutes. The 20% HPMC solution was then added and mixed at 1200 rpm with a magnetic stirrer for 3 minutes. Two hours after HPMCAS slurry addition in formulation, magnetic stirring was decrease to 80 rpm for maturation overnight at room temperature.

Results

TABLE 16

| Example | Film | Viscosity (Brookfield) |
| --- | --- | --- |
| 48 | Transparent, brittle film | 792.8 cP at 21° C. (S27, 12 rpm) |

Example 49

In a beaker of 400 ml, 60 g of Aquacoat CPD 30 were placed at 150 rpm magnetic stirring at room temperature. After 30 minutes, 1.40 g of DEP were added at 150 rpm stirring at room temperature. Two hours later, 8.67 g of HPMCAS slurry were added. HPMCAS slurry comprised 78.43% of water pH4, 16.15% HPMCAS, 0.81% Eudragit E PO and 4.61% of a 20% HPMC solution. HPMCAS and Eudragit E PO were mixed and pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 400 rpm for 30 minutes. The 20% HPMC solution was then added and mixed at 1200 rpm with a magnetic stirrer for 3 minutes. Two hours after HPMCAS slurry addition in formulation, magnetic stirring was decrease to 80 rpm for maturation overnight at room temperature.

Example 50

In a beaker of 400 ml, 60 g of Aquacoat CPD 30 were placed at 150 rpm magnetic stirring at room temperature. After 30 minutes, 1.40 g of DEP were added at 150 rpm stirring at room temperature. Two hours later, 9.11 g of HPMCAS/TiO$_2$ slurry were added. HPMCAS/TiO$_2$ slurry comprised 74.64% of water pH4, 15.37% HPMCAS, 4.83% TiO$_2$, 0.77% Eudragit E PO and 4.39% of a 20% HPMC solution. HPMCAS, TiO$_2$ and Eudragit E PO were mixed and pre-dispersed in water pH 4 at 700 rpm magnetic stirring and let in these conditions for at least 30 minutes. Dispersion 3×2 minutes at 13 000 rpm with a high speed homogenizer was then performed. The slurry was allowed to defoam under magnetic stirring at 400 rpm for 30 minutes. The 20% HPMC solution was then added and mixed at 1200 rpm with a magnetic stirrer for 3 minutes. Two hours after HPMCAS slurry addition in formulation, magnetic stirring was decrease to 80 rpm for maturation overnight at room temperature.

Results

BPU test conditions: pin temperature: 60° C.; formulation temperature: 21° C., drying 30 minutes at 60° C. in an oven.

TABLE 17

| | | | BPU test | |
| --- | --- | --- | --- | --- |
| Example | Film | Viscosity (Brookfield) | Pick-up and setting properties | Capsule film |
| 49 | Transparent film | 841.6 cP at 21° C. (S27, 12 rpm) | Slight over pick-up and correct setting | Transparent film |
| 50 | White opaque film | 646.1 cP at 21° C. (S27, 12 rpm) | Slight over pick-up and correct setting | White opaque film |

As discussed above, existing process to obtain hard capsules with controlled release properties, e.g., double dipping techniques or post-manufacturing techniques, require the use of multiple steps, which is contrary to the present disclosure. Without wanting to be bound by any theory, it is believed that the processes described herein entail coalescence of the aqueous composition on the surface of a conventional pin, assisted by a thermo-gelling phenomenon due to the use of the processing aid that is able to form thermo-reversible gels at elevated temperature. Thus, evaporation of water occurs while boundaries between polymer dispersed particles disappear, and the particles close-pack and lead to an uniform phase domain. With continuing evaporation and particle compaction, a polymer film starts forming with compacted controlled release polymer particles, leading to inter-particles diffusion of controlled release polymer molecules that generate isotropic polymer film. Thus, the present disclosure provides processes, wherein hard capsule shells can be obtained that display, for example bulk enteric properties, or other controlled release properties without the need to repeatedly (e.g. double) dip the pins or apply further external enteric coatings to the already manufactured shells.

Furthermore, the present disclosure also accomplishes, in part, the use of aqueous compositions comprising an aqueous dispersion of controlled release polymers; the use of aqueous compositions as opposed to non-aqueous (or solvent-based) polymer solutions, together with processing aids; the production of films on the moulding pins surface by inducing coalescence of controlled released polymer dispersed particles in contrast to polymer gelification; the ability to use of higher amounts of controlled release polymer; and increased viscosity of the aqueous compositions described herein that is otherwise unattainable by Different processes outside the scope of the present disclosure.

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A capsule shell comprising:
 a non-salified, enteric functional polymer, the functional polymer selected from the group consisting of cellulose acetate phthalate and hydroxypropyl methylcellulose acetate succinate, the functional polymer being present in an amount of about 50% or greater by weight of the total weight of the shell;

at least one processing aid present in an amount ranging from about 0.5% to about 49% by weight of the total weight of the shell, wherein at least one processing aid comprises poloxamer 188; and water present in an amount ranging from about 1% to about 20% by weight over the total weight of the shell.

2. The capsule shell according to claim 1, wherein said capsule shell is a hard capsule shell.

3. The capsule shell according to claim 1 wherein the processing aid is a plasticizer present in an amount ranging from about 6% to about 20% of the total weight of the shell.

4. The capsule shell according to claim 1 wherein the processing aid further comprises acetyl triethyl citrate.

5. The capsule shell according to claim 1, further comprising at least one encapsulated active ingredient.

6. The capsule shell according to claim 1, wherein the functional polymer comprises cellulose acetate phthalate and hydroxypropyl methylcellulose acetate succinate.

7. The capsule shell according to claim 1, wherein the capsule shell further comprises copolymerisate of methacrylic acid and either methylmethacrylate or ethyl acrylate.

8. The capsule shell according to claim 1, wherein said capsule shell is manufactured with an aqueous composition comprising:

an aqueous dispersion of a functional polymer, said polymer being present in an amount ranging from about 5% to about 50% by weight of the total weight of said aqueous composition;

at least one processing aid present in an amount ranging from about 0.5% to about 20% by weight of the total weight of said aqueous composition; and water.

9. A capsule shell comprising:

at least one non-salified functional polymer, the functional polymer being an enteric polymer selected from cellulose acetate phthalate and/or hydroxypropyl methylcellulose acetate succinate, the functional polymer being present in an amount of about 50% or greater by weight of the total weight of the shell;

at least one processing aid comprising poloxamer 188 present in an amount of at least 0.5% by weight of the total weight of the shell;

a copolymerisate of methacrylic acid and either methylmethacrylate or ethyl acrylate; and water present in an amount ranging from about 1% to about 20% by weight over the total weight of the shell.

10. The capsule shell according to claim 9, wherein the functional polymer comprises cellulose acetate phthalate and hydroxypropyl methylcellulose acetate succinate.

* * * * *

UNITED STATES PATENT AND TRADEMARK OFFICE
CERTIFICATE OF CORRECTION

PATENT NO. : 10,525,010 B2  
APPLICATION NO. : 14/398177  
DATED : January 7, 2020  
INVENTOR(S) : Benameur et al.

Page 1 of 1

It is certified that error appears in the above-identified patent and that said Letters Patent is hereby corrected as shown below:

In the Specification

Column 3, Line 17, "aqueous composition s" should read --aqueous compositions--.

Column 4, Line 11, "even or" should read --event or--.

Column 8, Line 16, "aid is present" should read --aid present--.

Column 13, Line 25, "of the drying step" should read --the drying step--.

Column 22, Line 45, "at room." should read --at room temperature.--.

Column 30, Line 33, "an uniform" should read --a uniform--.

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*